(12) United States Patent
Hinding et al.

(10) Patent No.: US 12,114,835 B2
(45) Date of Patent: Oct. 15, 2024

(54) ILLUMINATION DEVICE WITH LIGHT GUIDE DETECTION

(71) Applicant: KARL STORZ SE & Co. KG, Tuttlingen (DE)

(72) Inventors: Thomas Hinding, Tuttlingen (DE); Bernhard Gloeggler, Tuttlingen (DE); Werner Goebel, Tuttlingen (DE); Teresa Pfau, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 31 days.

(21) Appl. No.: 17/388,435

(22) Filed: Jul. 29, 2021

(65) Prior Publication Data

US 2022/0061638 A1 Mar. 3, 2022

(30) Foreign Application Priority Data

Sep. 3, 2020 (DE) ...................... 10 2020 123 031.1

(51) Int. Cl.
*A61B 1/06* (2006.01)
*A61B 1/00* (2006.01)
*A61B 1/04* (2006.01)
*A61B 1/07* (2006.01)

(52) U.S. Cl.
CPC ...... *A61B 1/00126* (2013.01); *A61B 1/00117* (2013.01); *A61B 1/04* (2013.01); *A61B 1/0669* (2013.01); *A61B 1/0684* (2013.01); *A61B 1/07* (2013.01)

(58) Field of Classification Search
CPC ............ A61B 1/00011; A61B 1/00013; A61B 1/00016; A61B 1/00018; A61B 1/00117; A61B 1/00126; A61B 1/0661; A61B 1/0669; A61B 1/0684; A61B 1/07;
(Continued)

(56) References Cited

U.S. PATENT DOCUMENTS 5,830,138 A * 11/1998 Wilson ............... A61B 5/14539
600/327
2005/0140270 A1 6/2005 Henson et al.
(Continued)

FOREIGN PATENT DOCUMENTS

DE 102013113511 A1 6/2015

*Primary Examiner* — Ryan N Henderson
(74) *Attorney, Agent, or Firm* — Jason H. Vick; Womble Bond Dickinson (US) LLP

(57) ABSTRACT

An illumination device for an endoscope includes illumination means for coupling light into a light guide. The illumination means has an LED matrix array having a plurality of LED pixels forming an emission area, and further includes a light guide port associated with the illumination means for positioning a light-guiding transmission area, which is disposed at an end of the light guide. The device also includes LED pixels configured as sensor elements configured to detect LED pixels of the emission area that are directed at non-light-guiding portions of the light guide, and wherein the device has a control unit which is configured to selectively operate the LED pixels of the LED matrix array for coupling light into the light guide in such a manner that at least some of the LED pixels directed at the non-guiding portions of the light guide in the main emission direction are operated at lower power or deactivated.

16 Claims, 7 Drawing Sheets

(58) Field of Classification Search
CPC ............ G02B 23/0661; G02B 23/0669; G02B 19/0061; G02B 19/0066
See application file for complete search history.

(56) References Cited

U.S. PATENT DOCUMENTS

2011/0257483 A1* 10/2011 Mizuyoshi ......... G02B 23/2469
362/555
2015/0185414 A1  7/2015 Baumann

* cited by examiner

ILLUMINATION DEVICE WITH LIGHT GUIDE DETECTION

CROSS-REFERENCE TO RELATED APPLICATIONS

This application claims the benefit under 35 U.S.C. 119(a) to German Patent Application No. 10 2020 123 031.1, filed 3 Sep. 2020, the disclosure of which is incorporated herein by reference in its entirety.

The present invention relates to an illumination device for an endoscope, the device comprising integrated detection means for light guide detection, and to a method for operating the illumination device.

In modern endoscopy, the provision of a light source for illumination is essential when examining cavities that are generally difficult to access. In addition to the provision of a light source at a distal end of an endoscope for insertion into the cavity to be examined, it is well known for an external light source or an illumination device having said light source to be provided and for light to be transmitted via a proximal end of the endoscope by means of a light guide having light-guiding fibers disposed therein to the distal end, i.e., to the tip of the endoscope, where the light exits in order to illuminate the cavity. In addition to a smaller structural shape of the endoscope, this has the advantage that a greater introduction of heat into the cavity to be examined is avoided.

Aside from halogen bulbs or arc lamps, it is also known for light emitting diodes (LEDs) to be provided as light sources in the illumination device. The light provided by the illumination device is typically coupled into the light guide connected or connectable to the endoscope at a light guide port to be provided, such as a plug-in coupling.

The light sources known so far and the illumination devices equipped with them are usually adapted to the light guide to be connected thereto. In particular, an emission area of the light source is adapted to the transmission area of the light guide to be connected thereto. This allows a simple and in particular energy-efficient design of the illumination device. At the same time, however, this leads to a limitation of the possible uses, in particular since different light guides and endoscopes are employed depending on the intended use and as a function of anatomical factors. For example, light guides having a diameter of 4.8 mm are preferably used in laparoscopy, whereas considerably thinner light guides are used in otoscopy.

DE 10 2013 113 511 A1 discloses an endoscope comprising a fiber-optic bundle for transmitting light from a proximal end to a distal end, the proximal end having a continuous fiber-optic bundle and the distal end having multiple arbitrarily distributed sub-bundles or individual fibers. Light is coupled in by means of an array-type LED light source associated with the proximal end and comprising individual light sources, the arbitrary distribution of the sub-bundles and the thus achievable distribution of the activated individual light sources having the purpose of optimizing the heat distribution in the light source. The individual light sources are operated by a control unit using an assignment function, which determines the assignment between individual sub-bundles to the proximal end faces of the fibers, which are assigned to the respective individual light sources. The assignment function is determined using a separate test device when assembling the endoscope, the test device having external photodiodes for detecting a respective light exit at the distal end of the sub-bundles of the endoscope.

US 2011/0257483 A1 discloses a device having an LED matrix light source, a focusing unit associated with the latter, and a light guide of an endoscope disposable relative to an emission area of the focusing unit. A control unit associated with the LED light source is configured in such a manner that it reads out a memory in a respective endoscope and operates the light source based thereon.

US 2005/0140270 A1 discloses an illumination unit having an LED matrix array comprising a plurality of LED light sources and a light guide associated with the latter, the light guide being stabilized by a provided support structure between its first end and its second end, and the device having a heat sink thermally coupled to a conductor layer of the LED light sources.

Based on the known state of the art, the object of the present invention is to provide an illumination device and a method for operating an illumination device for an endoscope which addresses the above disadvantages of the state of the art. In particular, an improved illumination device and a method for operating an illumination device which allows extended usability while being of an energy-efficient and simple design are to be provided.

This object is attained by the device and the method according to the independent claims. The dependent claims describe advantageous embodiments of the present invention. Moreover, the invention addresses other problems, as apparent from the following description.

In a first aspect, the invention relates to an illumination device for an endoscope, the device comprising illumination means for coupling light into a light guide connectable to the device, the illumination means comprising an LED matrix array comprising a plurality of LED pixels forming an emission area, the device comprising a light guide port associated with the illumination means for positioning a light-guiding transmission area, which is disposed at an end of the light guide, essentially orthogonally to a main emission direction of the emission area of the LED matrix array, wherein the device comprises detection means which are configured to detect LED pixels of the emission area that are directed at non-light-guiding portions of the light guide in the main emission direction, and wherein the device has a control unit which is configured to selectively operate the LED pixels of the LED matrix array for coupling light into the light guide in such a manner that at least some of the LED pixels directed at the non-guiding portions of the light guide in the main emission direction are operated at lower power or deactivated.

The provided device allows non-light-guiding portions of a light guide disposed on the illumination device to be detected and thus different light guides to be detected with respect to their transmission area or with respect to their non-light-guiding portions surrounding the transmission area. Thus, the individual LED pixels can be selectively, i.e., individually, operated for light emission when light is being coupled into the light guide, at least some of the LED pixels directed at non-guiding portions of the light guide being operated at lower power or deactivated. In this way, the introduction of light into non-light-guiding portions and thus an undesired thermal load on the light guide and in particular on a typically metallic plug of the light guide being reduced or avoided. Additionally, an energy-efficient operation of the illumination device is made possible since the light source can be ideally exploited for the given light guide connected thereto, and not only the provision of an insufficient light-emitting emission area for the connected light guide but in particular also the provision of an excessively large light-emitting emission area is avoided. A cooling for the light guide or the light guide plug, which may otherwise have to be provided, can also be avoided, which allows a simple and space-saving design of the illumination device to be achieved in addition to the advantages mentioned above.

In the following, the term "LED matrix array" refers to an LED matrix array comprising a plurality of LED pixels which are disposed thereon in particular in the shape of a grid and which can be individually operated. They are advantageously formed by individual white-light-emitting LED chips. The LED matrix array preferably comprises between 500 and 4500, more preferably between 1000 and 4500 LED pixels. The individual LED pixels form a continuous emission area of the LED matrix array. At least some of the respective LED pixels are preferably configured to be operated individually in terms of their light intensity or their light emission. This can take place by commonly known control methods, such as pulse-width modulation.

In the following, the term "main emission direction" of the emission area refers to a direction which is orthogonal to the emission area formed by the LED pixels and in which the LED pixels emit light.

In the following, the term "non-light-guiding portions" of the light guide in particular refers to parts of the light guide that guide significantly less light than a light-guiding transmission area and parts that guide essentially no light. These comprise in particular a light guide plug disposed at an end of the light guide and a light guide sleeve surrounding the continuous, light-guiding transmission area. Preferably, the non-light-guiding portions are in particular portions of the light guide that reflect light in a direction opposite to a main emission direction of the emission area. The transmission area of the light guide is preferably composed of a plurality of light-guiding fiber ends which are disposed essentially orthogonal to a main emission direction of the emission area for coupling in light.

The expression "directed" at a non-light-guiding portion in particular means that the emitted radiation of the respective LED pixel in the main emission direction strikes at least a portion of a non-light-guiding portion. This preferably means that at least a portion, preferably at least 30%, more preferably at least 50% of the respective LED pixel is obstructed or covered by a non-light-guiding portion of the light guide in a top view of the emission area along the main emission direction.

In a preferred embodiment, the control unit is configured to deactivate all LED pixels directed at a non-light-guiding portion of the light guide in the main emission direction when light is being coupled into the light guide. In this way, an undesired introduction of heat into non-light-guiding portions of the light guide can be avoided and the efficiency of the coupling in of light can be optimized further.

In a preferred embodiment, the control unit is configured to detect a non-light-guiding outer contour of the light guide surrounding the transmission area based on information provided by the detection means. The information provided can in particular comprise a spatial arrangement of the LED pixels directed at the non-light-guiding portions in the emission area. In this context, the control unit is preferably configured to selectively or individually, operate the LED pixels as a function of the detected outer contour in such a manner that at least some, more preferably all of the LED pixels directed at the outer contour and/or at an area radially outside of the outer contour in the main emission direction are operated at lower power or deactivated when light is being coupled in.

In this way, an emission of light by the LED matrix array in the direction of the outer contour of the light guide and/or at an area radially outside of the outer contour of the light guide can be reduced or avoided, thus reducing an undesired introduction of heat into the light guide and allowing a more efficient operation of the device during the injection of light into the light guide.

In another preferred embodiment, the controller is alternatively or additionally configured to detect a continuous transmission area of the light guide connected to the light guide port based on the information provided by the detection means, in particular with respect to a spatial arrangement of the LED pixels in the emission area that are directed at the non-light-guiding portions. In this context, the control unit is preferably configured to selectively or individually, operate the LED pixels as a function of the detected continuous transmission area in such a manner that only the LED pixels that are directed at the transmission area in the main emission direction are operated for light emission when light is being coupled into the light guide. The remaining LED pixels will at least be operated at lower power or deactivated.

In another preferred embodiment, the controller can alternatively or additionally be configured to detect at least two and preferably a plurality of different outer contours of a light guide based on the information provided by the detection means, in particular with respect to a spatial arrangement of the LED pixels in the emission area that are directed at the non-light-guiding portions. In this context, the control unit can be configured to selectively or individually, operate the LED pixels for light emission as a function of the respective detected outer contour according to a spatial arrangement of the LED pixels on file or stored in the device when light is being coupled into the light guide. In this way, a transmission area of a light guide coded by the respective outer contour of the light guide can be decoded by the control unit, for example, and the emission area respectively the LED pixels of the emission area, can be operated in a manner adapted to the respective transmission area.

In a preferred embodiment, the illumination device has at least a first calibrating mode for detecting the LED pixels of the emission area that are directed at non-light-guiding portions of the light guide, and a second work operating mode for coupling light into the light guide. The control unit can be configured to sequentially and/or alternately activate the first and the second operating mode.

In this context, the control unit can be configured in such a manner that an activation of the device for example by means of a provided operating element is initially followed by an activation of the calibrating mode, in which the light guide connected to the device is detected by means of the detection means. In this process, in particular the LED pixels directed at non-light-guiding portions of the connected light guide are detected. Subsequently, the work operating mode is activated, in which the actual coupling in of light into the light guide by means of the illumination means and based on the individual operation of the LED pixels by the control unit takes place. The calibration preferably takes less than a second, more preferably less than 10 milliseconds.

An alternating activation of the first and the second operating mode can in particular comprise an activation of the calibrating mode at preferably regular intervals, such as every 30 seconds. In this way, the light guide detection can be continuously monitored and/or corrected for example in case the positioning of the light guide on or in the light guide port changes in particular because of external forces.

The detection means are preferably configured to detect reflected radiation occurring in particular in a direction opposite to the main emission direction of the emission area, in particular radiation reflected by non-light-guiding portions of the light guide. Thus, the detection means can detect radiation reflected by the non-light-guiding portions of the light guide in particular in a direction essentially opposite the main emission direction. The reflected radiation is in particular light radiation emitted by at least some of the LED pixels of the LED matrix array and reflected back by the non-light-guiding portions of the light guide.

In a preferred embodiment, the detection means are formed by at least some of the LED pixels of the LED matrix array which are configured to be operated as sensor elements by the control unit at least in a first calibrating mode of the device. Said LED sensor elements can be pure photodiodes which are configured to detect light incident on the respective LEDs and therefore to acquire sensor information by means of the control unit. In a particularly preferred embodiment, however, the respective LED pixels configured to be operated as sensor elements are configured in such a manner that they can be operated for light emission in a second work operating mode.

In order to operate the LED pixels which emit light in the work operating mode as sensor elements in the calibrating mode, the control unit is preferably configured in such a manner that the respective LED pixels are not supplied with current and/or voltage in the calibrating mode and are therefore not excited to emit light. Additionally, the control unit acquires a voltage signal and/or a current signal based on which the control unit can determine a respective incidence of reflected light on the respective LED pixel. In this context, the invention utilizes the property of the respective LED chips or LED pixels by which a current and/or voltage signal dependent on incident light can be detected at a shut-off LED or an LED not supplied with current or voltage when light is incident on said LED.

The control unit can have at least one microcontroller and associated memory means. Additionally, the control unit can be configured to execute a predefined analysis algorithm, which is configured for an individual operation of the LED pixels as sensor elements and/or as light emission elements.

The control unit is preferably configured to evaluate, and in particular compare signals of, all LED pixels operated as LED sensor elements. By evaluating the acquired sensor information or current and/or voltage signals accordingly, light laterally incident on the respective LED pixels from adjacent LED pixels excited to emit light can be filtered during calculation or evaluation. In other words, the control unit can differentiate which LED pixels are merely irradiated by LED pixels adjacent in the emission area and excited to emit light and which LED pixels are exposed to additional reflected radiation, in particular because of reflections occurring at non-light-guiding portions of the light guide in a direction essentially opposite to the main emission direction, by comparing the acquired sensor signals. The control unit can consequently identify the latter as LED pixels of the emission area that are directed at non-light-guiding portions in the main emission direction. These can be used as reference points on the emission area or in the LED matrix array for the individual operation of the emission area when light is being coupled into the light guide.

The control unit is preferably configured to operate at least a first part of the LED pixels of the LED matrix array for light emission and to operate at least a second part of the LED pixels of the LED matrix array as sensor elements for detecting reflected light incident on the respective LED pixels in the first calibrating mode. The first part of the LED pixels, which serve as emission elements, can comprise a number of LED pixels that is smaller than or essentially equal to that of the second part of the LED pixels, which serve as sensor elements.

The control unit can be configured to alternately operate the first part and the second part of the LED pixels as sensor elements and as light emission elements. In this way, the precision of the detection of LED pixels in the emission area that are directed at non-light-guiding portions can be improved further.

In a preferred embodiment, the control unit is configured to operate a plurality of LED pixels distributed on the emission area essentially evenly and/or according to a predefined calibration pattern as sensor elements. The LED pixels operated as sensor elements are preferably disposed in such a manner that they are distributed evenly between the LED pixels operated for light emission. This enables in particular an optimized detection of the LED pixels directed at non-light-guiding portions of the light guide. In another preferred embodiment, the control unit is configured to sequentially operate the LED pixels operated for light emission in a manner gradually widening radially outward from a center of the emission area, in particular essentially concentrically or in a star shape, in the first calibrating mode.

The control unit can be configured to operate at least every fourth, preferably every third LED pixel of the emission area in a row direction and/or in a column direction of the emission area of the LED matrix array as a sensor element. In another preferred embodiment, at least one LED pixel, preferably at least two LED pixels operated as sensor elements is/are disposed between two LED pixels adjacent in a row and/or a column direction and operated as emission elements.

In an alternative embodiment, the detection means can have optics, in particular a beam splitter or a semi-transparent mirror, disposed between the emission area and the transmission area of the light guide, and an associated sensor unit for detecting radiation reflected back by non-guiding portions of the light guide. The associated sensor unit can comprise a CCD camera or a photodiode array, which allows back reflections from non-light-guiding portions of the light guide to be reported back to the control unit.

The light guide port is preferably configured to position at least two light guides having differing transmission areas in a centered manner. The light guide port preferably has an in particular circular socket into which a plug disposed at an end of the light guide can be inserted. The plug preferably has a sleeve-like design which surrounds the transmission area disposed at the end for coupling light into the light guide. The plug preferably has a plane surface disposed parallel to the transmission area. The plug is preferably made of metal.

The device preferably has no cooling means for cooling the light guide and in particular the light guide plug.

In another aspect, the invention relates to the use of the illumination device as described above for coupling light into at least two light guides having transmission areas differing in size and/or shape for injecting light. The respective transmission areas preferably have a diameter between 1.5 and 14 mm, more preferably between 2 and 10 mm. The respective transmission areas are preferably each surrounded by a sleeve-like plug.

In another aspect, the invention relates to a method for coupling light into a light guide for an endoscope, the method comprising the following steps:

providing an illumination device comprising illumination means for coupling light into a light guide connectable to the device, the illumination means comprising an LED matrix array comprising a plurality of LED pixels forming an emission area, positioning a light-guiding transmission area, which is disposed at an end of a light guide, essentially orthogonally to a main emission direction of the emission area of the LED matrix array, wherein the method further comprises the following steps:

detecting LED pixels of the emission area that are directed at non-light-guiding portions of the light guide in the main emission direction, and coupling light into the light guide, with the LED pixels of the emission area being selectively operated for light emission, wherein at least some of the LED pixels directed at non-light-guiding portions are operated at lower power or are deactivated.

To avoid repetitions, reference is made to the illumination device according to the invention described above. The features disclosed for the device are intended to be disclosed and claimable for the method, and vice versa.

In a preferred embodiment, the detection comprises operating a first part of the LED pixels of the emission area for light emission and operating a second part of the LED pixels of the emission area as sensor elements for detecting reflected light incident on the respective LED pixels.

The detection preferably comprises operating the respective LED pixels in a varying manner as light emission elements or as sensor elements. The varying operation of the respective LED pixels can take place according to a predefined chronological order and/or a spatial arrangement of the respective LED pixels on the emission area. The operation can comprise an essentially chessboard-type or chessboard-shaped operation of a first part of the LED pixels for light emission and of a second part of the LED pixels as sensor elements. Alternatively or additionally, the operation can comprise operating a first part of the LED pixels for light emission in a manner widening radially outward from a center of the emission area, in particular essentially concentrically or in a star shape. The operation in question can be executed just once, twice, or multiple times according to a predefined sequence.

The detection can additionally comprise detecting an outer contour of the light guide by evaluating sensor data acquired by the LED pixels operated as sensor elements. In this context, the detection can take place based on the signals detected by the LED pixels directly and/or based on an interpolation executed by the control unit based on the detected signals.

When light is being coupled in, the LED pixels will be selectively operated in such a manner that at least some, preferably all of the LED pixels that are directed at the outer contour and/or at an area radially outside of the outer contour in the main emission direction are operated at lower power or deactivated.

Individual features, advantageous effects and details of the present invention are discussed below with reference to the purely schematic drawings, which are of an exemplary nature.

Figure 5A:
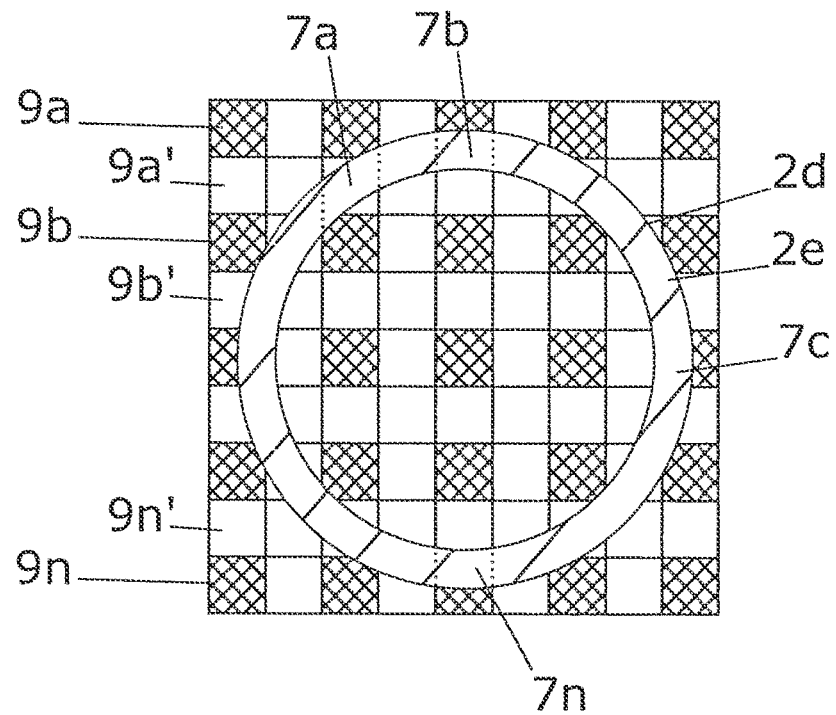
Figure 5B:
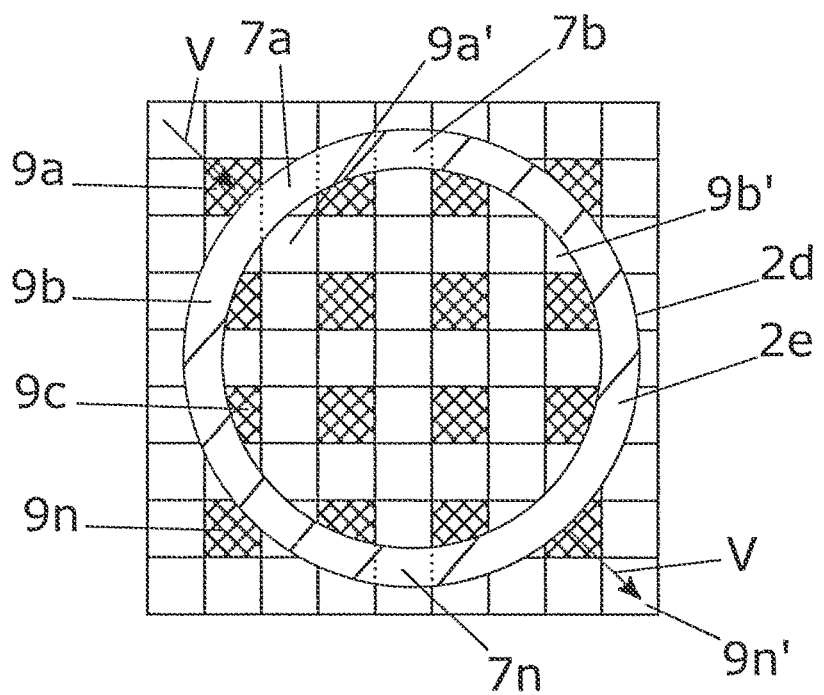
Figure 6A:
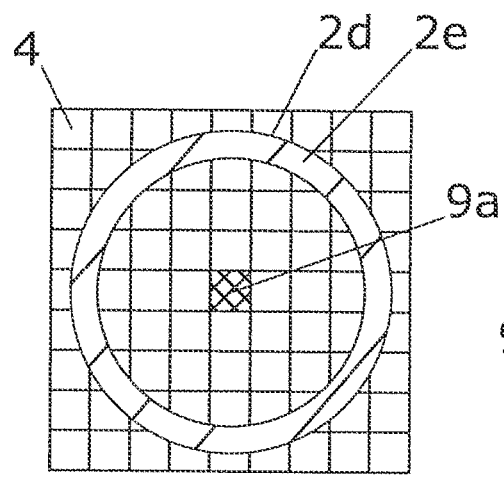
Figure 6B:
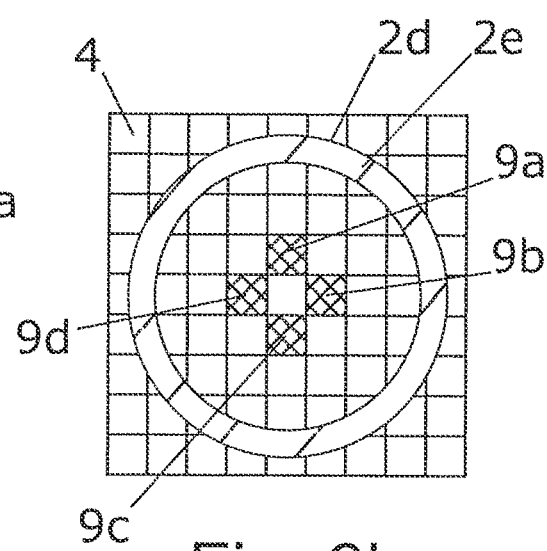
Figure 6C:
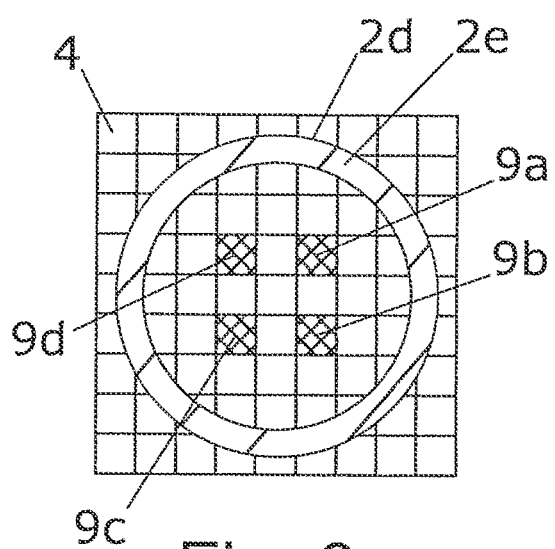
Figure 6D:
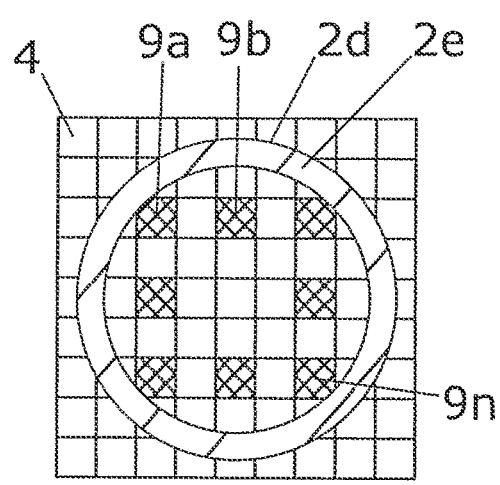
Figure 7A:
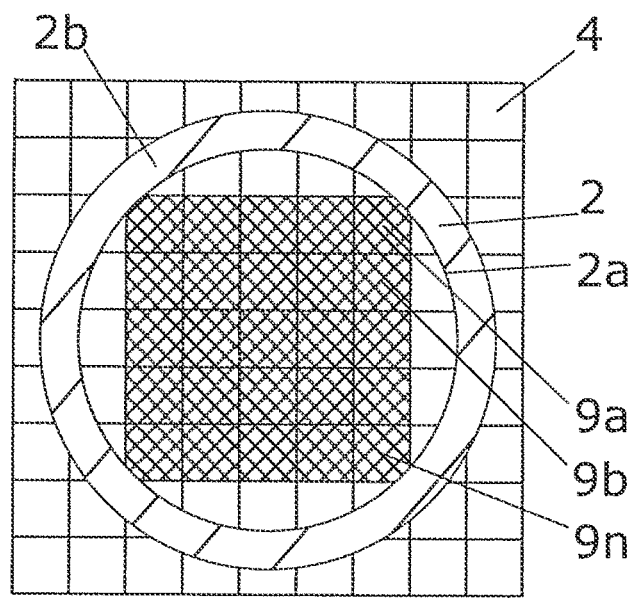
Figure 7B:
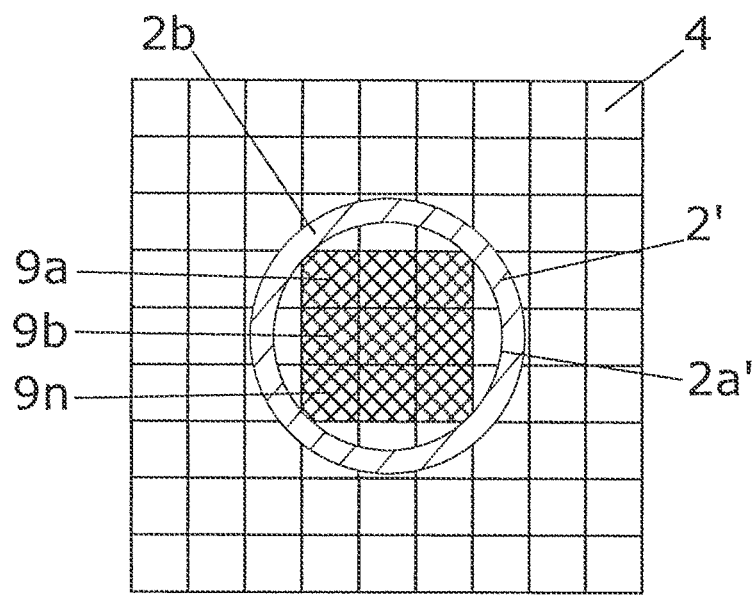
Figure 8A:
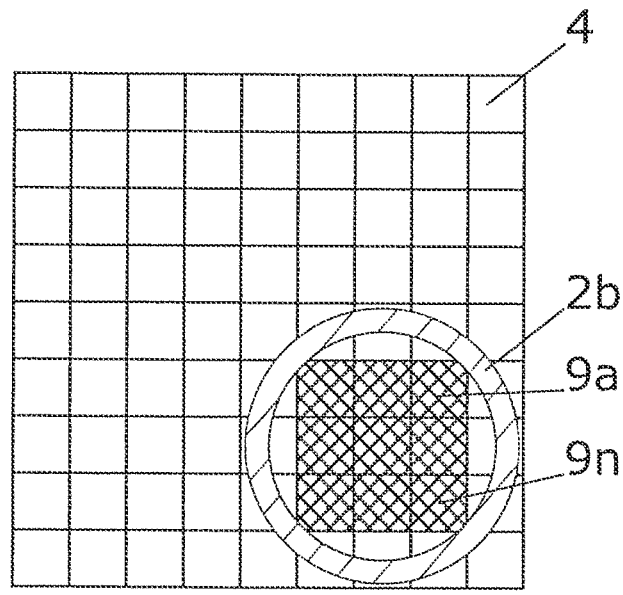
Figure 8B:
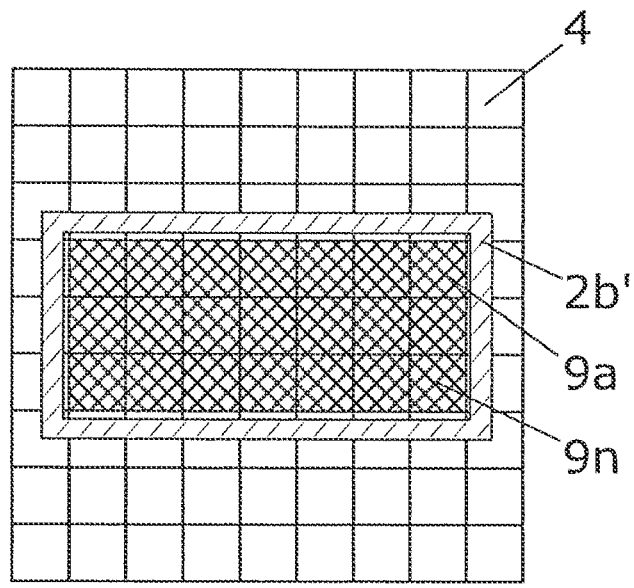
Figure 9:
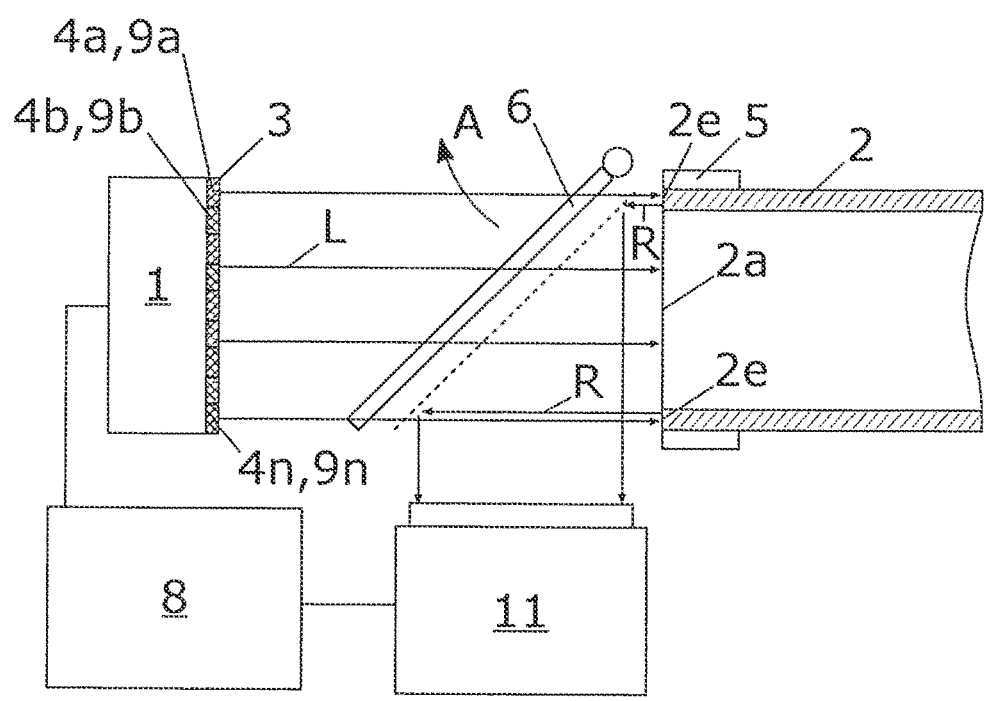

FIGS. 5a-b show a preferred embodiment of a calibrating mode of the device for detecting the light guide, with the sensor elements essentially disposed in a checkerboard pattern;

FIGS. 6a-d show another preferred embodiment of a calibrating mode of the device for detecting the light guide, with the light emission elements disposed in a manner widening radially outward;

FIGS. 7a-b are schematic top views of the illumination means when light guides are operated in different ways in the work operating mode for coupling light into the light guide;

FIGS. 8a-b are schematic top views of the illumination means when light guides having different outer contours are operated in different ways;

FIG. 9 shows another preferred embodiment of the device according to the invention, which has optics disposed between the emission area and the transmission area.

Figure 1:
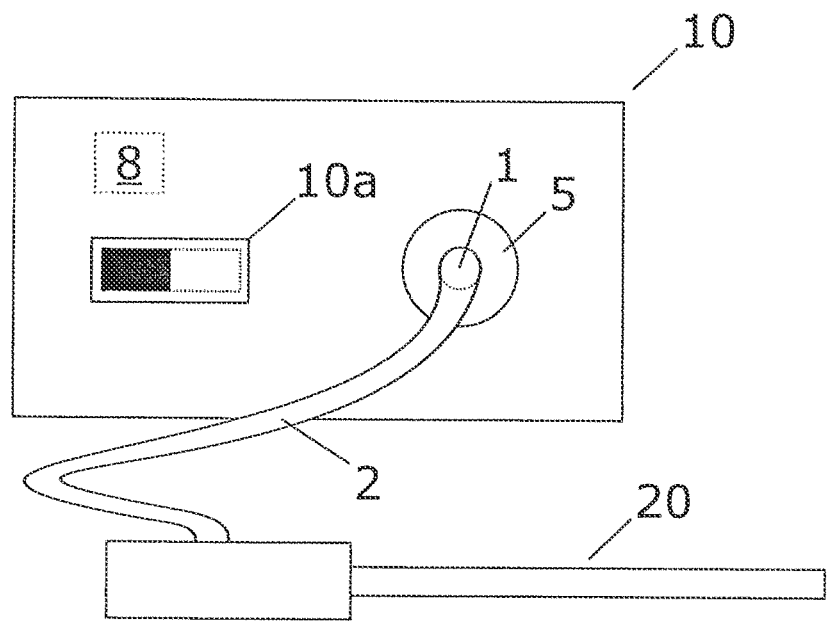
FIG. 1 is a front view of an illumination device according to a preferred embodiment of the invention.

FIG. 1 shows an illumination device 10 for an endoscope 20, device 10 comprising illumination means 1 for coupling light into a light guide 2 connectable to the device via a light guide port 5. Device 10 can comprise a user interface 10a, which can in particular comprise an on/off switch or a controller for light intensity. Device 10 further comprises a power supply (not shown) and a control unit 8 at least connected to the power supply and to illumination means (see FIG. 2b) associated with light guide port 5. Light guide 2 can be permanently connected to endoscope 20 or can be configured to be screwed to the endoscope, in particular via a screw cap.

Figure 2A:
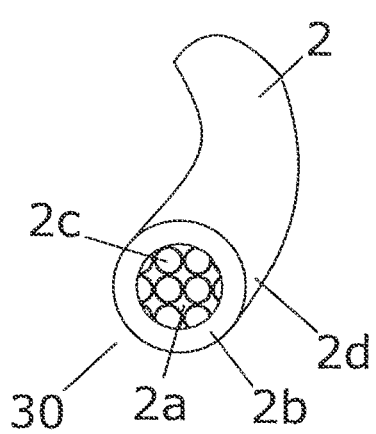
FIG. 2a is a schematic detail view of a light guide for being connected to the illumination device.

FIG. 2a schematically shows a connector or plug area 30 at an end of light guide 2 and configured to be connected to illumination device 10. It comprises a circular transmission area 2a, which is formed by a plurality of fiber ends 2c disposed therein. Transmission area 2a is surrounded or enclosed by a non-light-guiding outer contour 2b, which is sleeve-shaped in the case at hand and which is formed by a light guide sleeve 2d surrounding the optical fibers of the light guide. Light guide sleeve 2d is preferably plane in the connector or plug area. Plug area 30 and preferably also plane outer contour 2b are preferably made of metal, in particular polished metal.

Figure 2B:
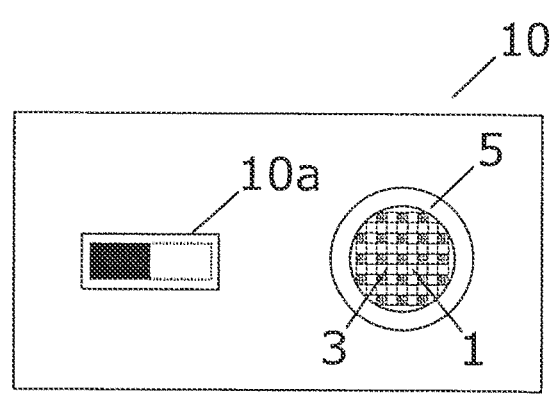
FIG. 2b is a detail view of the device without a connected light guide.
Figure 3:
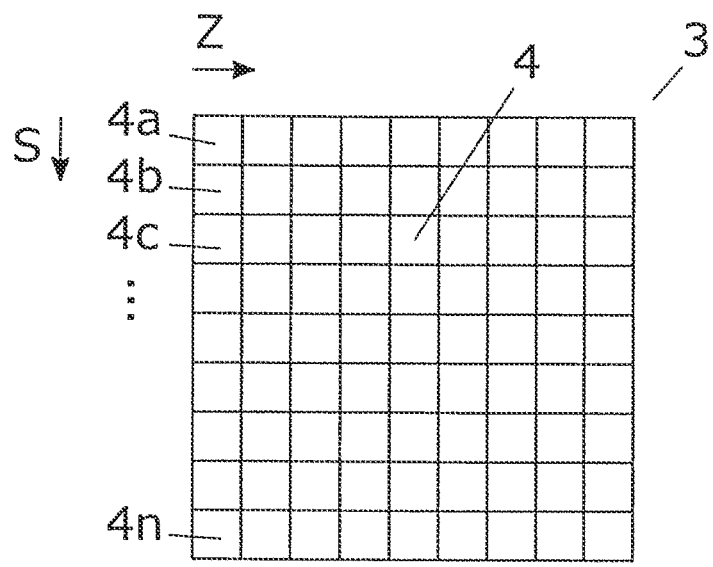
FIG. 3 is a schematic top view of an LED matrix array of the illumination means of the device.

FIG. 2b shows a front view of device 10 without a connected light guide 2. Illumination means 1 comprise an LED matrix array 3 disposed centrally relative to light guide port 5. FIG. 3 shows a schematic detail view of LED matrix array 3, which has a plurality of individual LED pixels 4a, . . . , 4n, which are in particular disposed in a grid, i.e., in a row direction Z and a column direction S, and which form a continuous emission area 4.

Figure 4:
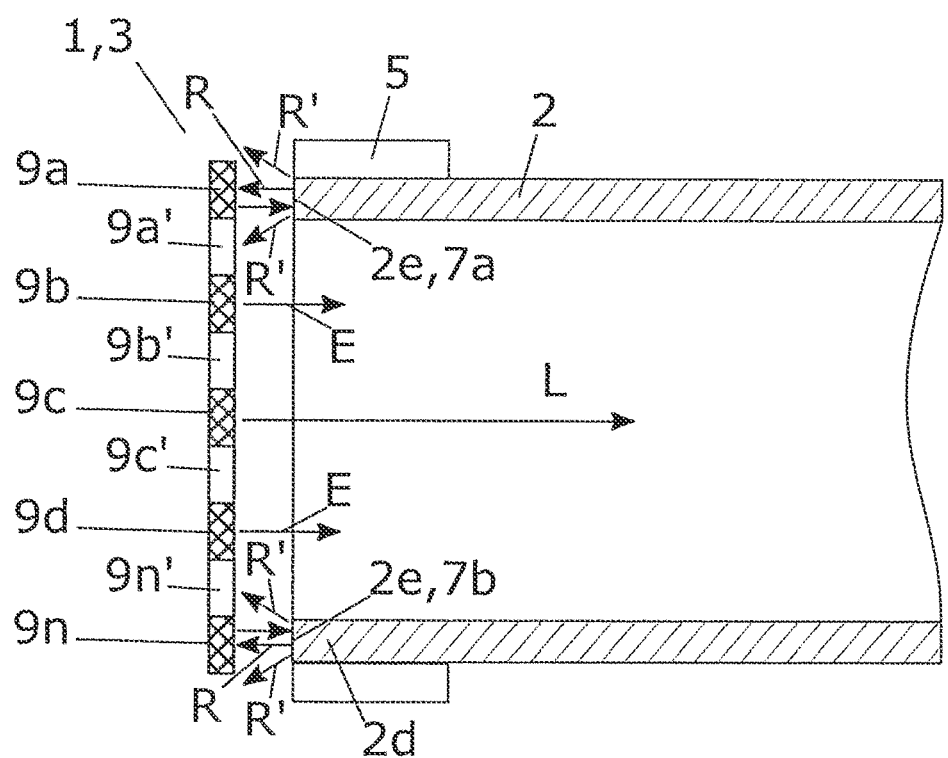
FIG. 4 is a schematic side view of a coupling of a light guide to the illumination means at the light guide port of the device.

FIG. 4 shows a schematic side view of a coupling of a light guide 2 to illumination means 1 at light guide port 5 of device 10. When light guide 2 is connected, its transmission area 2a is preferably disposed essentially parallel to emission area 4 of LED matrix array 3. A main emission direction L of emission area 4 is thus disposed essentially orthogonal to transmission area 2a. An outer contour surface 2e disposed at an end of light guide sleeve 2d is preferably also disposed essentially parallel to emission area 4.

The Figure shows a first calibrating mode of the device for detecting the LED pixels of emission area 4 that are directed at non-light-guiding portions 7a, . . . , 7n of light guide 2. In the calibrating mode, control unit 8 is configured to operate at least a first part of LED pixels 9a, . . . , 9n of LED matrix array 3 for light emission E and to operate at least a second part of LED pixels 9a', ..., 9n' of LED matrix array 3 as sensor elements for detecting reflected light R incident on the respective LED pixels.

For the sake of simplification, the schematic drawing merely shows light emission E of the respective LED pixels in main emission direction L. As shown in FIG. 4, reflection R occurs at non-light-guiding portions 7a and 7b of light guide 2. Radiation R reflected back from there, which is essentially oriented in a direction opposite to main emission direction L, can then be detected by respective LED pixels 9a', ..., 9n' which are directed at non-light-guiding portions 7a and 7b and configured as sensor elements, and/or which are disposed adjacent to those LED pixels 9a, ..., 9n directed at non-light-guiding portions 7a and 7b and serving as emission elements. Hereby, in particular a current signal and/or a voltage signal occurring at sensor elements 9a', ..., 9n' because of the incident reflected light is tapped by the control unit. In this context, the occurring reflection R can comprise a direct reflection at the respective non-light-guiding portions 7a and 7b and at least partially also a diffuse reflection or diffuse reflected radiation R'. Diffuse reflected radiation R' refers to scattered back radiation in particular due to potential unevenness at a given surface of non-light-guiding portions 7a, 7b, ..., 7n of light guide 2.

Control unit 8 is preferably configured in such a manner that it operates respective LED pixels 4a, ..., 4n in a varying and/or alternating manner as emission elements 9a, ..., 9n and as sensor elements 9a', ..., 9n'. An example of such a configuration is shown in FIGS. 5a and 5b. Control unit 8 is configured to operate first LED pixels 9a, ..., 9n, which are operated as emission elements, and second LED pixels 9a', ..., 9n', which are operated as sensor elements, according to a predefined calibration pattern, which, as an example, is a chessboard-shaped configuration in the case at hand. For example, every other LED 4a, ..., 4n of emission area 4 in row direction Z and/or column direction S (see FIG. 3) can be operated as an emission element 9a, ..., 9n in order to provide light emission for detecting the non-light-guiding portions of connected light guide 2. The remaining LED pixels can be operated as sensor elements 9a', ..., 9n' in order to detect reflections on non-light-guiding portions 7a, ..., 7n of light guide 2, in particular on outer contour surface 2e of light guide sleeve 2d surrounding transmission area 2a. Non-light-guiding portions 7a, ..., 7n are schematically illustrated as mere examples in FIGS. 5a and 5b. Non-light-guiding portions 7a, ..., 7n preferably form the outer contour surface 2e of light guide 2.

After the emission and the detection has taken place in the configuration shown in FIG. 5a, a varying operation of individual LED pixels 4a, ..., 4n can take place, as shown in FIG. 5b. In doing so, the chessboard-shaped operation of the individual LED pixels is offset or shifted parallel or diagonally by an offset V relative to the configuration in FIG. 5a. This means that LED pixels previously operated as sensor elements 9a', ..., 9n' will now be operated as emission elements 9a, ..., 9n and vice-versa. Control unit 8 again detects the current and/or voltage signals occurring at each of sensor elements 9a', ..., 9n' because of incident reflected light R.

Control unit 8 can be configured to compare the signals of all LED pixels 9a', ..., 9n' operated as sensor elements. By comparing the acquired sensor signals, control unit 8 can preferably differentiate between LED pixels that serve as sensor elements and are merely irradiated by emission elements 9a, ..., 9n disposed adjacent in emission area 4 and LED pixels that serve as sensor elements and are exposed to additional reflected radiation R, in particular because of reflections R on non-light-guiding portions 7a, ..., 7n of light guide 2 that occur in a direction essentially opposite to main emission direction L. Control unit 8 can consequently identify the latter as LED pixels of emission area 4 that are directed at non-light-guiding portions in main emission direction L. They can be used as reference points on emission area 4 or in LED matrix array 3 for individually operating emission area 4 when light is being coupled into light guide 2.

FIGS. 6a to 6d show an alternative embodiment, in which LED pixels 4a, ..., 4n are operated in the calibrating mode in such a manner that an arrangement of respective LED pixels 9a, ..., 9n operated for emission is provided which gradually widens outward and preferably radially from a center of the emission area. The remaining LED pixels can be operated as sensor elements 9a', ..., 9n'.

FIGS. 7a and 7b show a schematic top view of illumination means 1 during the differing operation of light guides 2 and 2' with differing transmission areas 2a and 2a' in the work operating mode. The work operating mode of device 10 corresponds to the operation for coupling light into light guides 2 and 2' each connected to the device. The previously performed calibration allows control unit 8 to detect LED pixels of emission area 4 that are directed at non-light-guiding portions of light guide 2. They are preferably operated at lower power or more preferably deactivated in the work operating mode. Remaining LED pixels 9a, ..., 9n are operated for light emission at a predefined power that can optionally be set by the user.

Control unit 8 preferably further detects an outer contour 2b of light guide 2 connected to the device when in the calibrating mode and operates at least some of the LED pixels directed at outer contour 2b and/or at an area radially outside of outer contour 2b in main emission direction L at lower power or deactivates them during the coupling in of light in the work operating mode.

FIGS. 8a and 8b schematically show an example of a detection of a given outer contour 2b of a connected light guide. As shown in FIG. 8a, control unit 8 can be configured to detect a shift or an offset of light guide 2 relative to emission area 4 due to external forces, for example. This can take place by alternating activation of the calibrating mode and the work operating mode described above. In particular, the calibrating mode can be activated at regular intervals during the work operating mode. The operation of emission area 4 can be adapted accordingly in the subsequent work operating mode.

FIG. 8b shows a mere example of the detection of a varying outer contour 2b' of a light guide 2, which differs from the outer contour shown before in that it has a polygonal contour. The controller can optionally be configured to detect at least two and preferably a plurality of different outer contours 2b, 2b' of a light guide 2 based on the information provided by the detection means, in particular information on a spatial arrangement of the LED pixels in the emission area that are directed at the non-light-guiding portions. In this case, the control unit can be configured to individually operate the LED pixels as a function of the detected outer contour according to a spatial arrangement of the LED pixels, on-file or stored in the device, for light emission during coupling of light into the light guide.

FIG. 9 shows an alternative embodiment of device 10 according to the invention. Herein, the detection means comprise optics 6, in particular a beam splitter or a semi-transparent mirror, which are disposed between emission area 4 and transmission area 2a of light guide 2, and an associated sensor unit 11 for detecting radiation R reflected back by non-guiding portions 7a, . . . , 7n of light guide 2. Sensor unit 11 can comprise a CCD camera or a photodiode array.

In the calibrating mode, the part of the emitted light that is reflected back by the non-light-guiding portions of light guide 2 is detected by associated sensor unit 11 via the optics, such as the semi-transparent mirror. In doing so, in particular a relative position of the respective back radiation R can be detected. Based on said detection, the respective LED pixels 4a, . . . , 4n can be operated accordingly in the work operating mode, as described above for the other embodiments. In the work operating mode, optics 6 can additionally be removed from the emission area of the illumination means 1, for example by pivoting (direction A).

REFERENCE SIGNS 1 illumination means
2 light guide
2a transmission area
2b outer contour
2c light-guiding fibers
2d light guide sleeve
2e outer contour surface
3 matrix array
4 emission area
4a, . . . , 4n LED pixels
5 light guide port
6 optics
7a, . . . , 7n non-light-guiding parts of the light guide
8 control unit
9a, . . . , 9n emission element
9a', . . . , 9n' sensor element
10 device
10a user interface
11 sensor unit
20 endoscope
30 plug area
A pivoting direction
E emission radiation
L main emission direction
R, R' reflected radiation
S column direction
V offset
Z row direction

The invention claimed is:

1. An illumination device configured for an endoscope, the device comprising:
   illumination means for coupling light into a light guide connectable to the device, the illumination means comprising an LED matrix array comprising a plurality of LED pixels forming an emission area,
   a light guide port associated with the illumination means for positioning a light-guiding transmission area, which is disposed at an end of the light guide, essentially orthogonally to a main emission direction of the emission area of the LED matrix array,
   LED pixels configured as sensor elements which are configured to detect LED pixels of the emission area that are directed at non-light-guiding portions of the light guide in the main emission direction, and
   a control unit coupled to the LED matrix array and to the LED pixels configured as sensor elements and configured to selectively operate the LED pixels of the LED matrix array for coupling light into the light guide in such a manner that at least some of the LED pixels directed at the non-guiding portions of the light guide in the main emission direction are operated at lower power or deactivated.

2. The illumination device according to claim 1, wherein the control unit is configured to detect a non-light-guiding outer contour of the light guide surrounding the transmission area based on information provided by the LED pixels configured as sensor elements, and that the control unit is configured to selectively operate the LED pixels as a function of the detected outer contour in such a manner that at least some of the LED pixels directed at the outer contour and/or at an area radially outside of the outer contour in the main emission direction are operated at lower power or deactivated during illumination of the LED pixels.

3. The illumination device according to claim 1, wherein the illumination device comprises at least a first calibrating mode for detecting the LED pixels of the emission area that are directed at non-light-guiding portions of the light guide and a second work operating mode for coupling light into the light guide, and that the control unit is configured to sequentially and/or alternately activate the first and the second operating mode.

4. The illumination device according to claim 1, wherein the LED pixels configured as sensor elements are configured to detect reflected radiation occurring in a direction opposite to the main emission direction of the emission area or radiation reflected by non-light-guiding portions of the light guide.

5. The illumination device according to claim 1, wherein the LED pixels configured as sensor elements are formed by at least some of the LED pixels of the LED matrix array which are configured to be operated as sensor elements by the control unit at least in a first calibrating mode of the device and to be operated for light emission at least in a second work operating mode.

6. The illumination device according to claim 5, wherein the control unit is configured to operate at least a first part of the LED pixels of the LED matrix array for light emission in the first calibrating mode and to operate at least a second part of the LED pixels of the LED matrix array as sensor elements for detecting reflected light incident on the respective LED pixel.

7. The illumination device according to claim 6, wherein the control unit is configured to alternately operate the first and the second part of the LED pixels as sensor elements and as light emission elements.

8. The illumination device according to claim 5, wherein the control unit is configured to operate a plurality of LED pixels distributed on the emission area essentially uniformly and/or according to a pre-defined calibrating pattern as sensor elements.

9. The illumination device according to claim 5, wherein the control unit is configured to operate at least every fourth or every third LED pixel of the emission area in a row direction and/or a column direction of the emission area of the LED matrix array as a sensor element.

10. The illumination device according to claim 5, wherein the control unit in the first calibrating mode is configured to sequentially operate the LED pixels operated for light emission in a manner gradually widening radially outward from a center of the emission area, or in an essentially concentrically or in a star shape.

11. The illumination device according to claim 1, wherein the LED pixels configured as sensor elements comprise optics including a beam splitter or a semi-transparent mirror, disposed between the emission area and the transmission area of the light guide, and an associated sensor unit including a CCD camera or a photodiode array, configured to detect radiation reflected back by non-guiding portions of the light guide.

12. The illumination device according to claim 1, wherein the LED matrix array comprises between 500 and 4500 pixels, which are formed by white light emitting LED chips.

13. The illumination device according to claim 1, wherein the light guide port is configured to position at least two light guides having different transmission areas.

14. The illumination device according to claim 1, adapted for coupling light into at least two light guides having transmission areas differing in size and/or shape.

15. An endoscopic illumination device comprising:
an LED matrix array comprising a plurality of LED pixels forming an emission area, the LED matrix array configured to couple light into a light guide connectable to the device,
a light guide port associated with the LED matrix array configured to position a light-guiding transmission area, which is disposed at an end of the light guide, orthogonally to a main emission direction of the emission area of the LED matrix array,
wherein the LED matrix array comprises LED sensor pixels configured to detect LED pixels of the emission area that are directed at non-light-guiding portions of the light guide in the main emission direction, and
a control unit coupled to the LED matrix array and to the LED sensor pixels and configured to selectively operate the LED pixels of the LED matrix array for coupling light into the light guide in such a manner that at least some of the LED pixels directed at the non-guiding portions of the light guide in the main emission direction are operated at lower power or deactivated.

16. The illumination device according to claim 15, wherein one or more of:
the control unit is configured to detect a non-light-guiding outer contour of the light guide surrounding the transmission area based on information provided by the LED sensor pixels, and that the control unit is configured to selectively operate the LED pixels as a function of the detected outer contour in such a manner that at least some of the LED pixels directed at the outer contour and/or at an area radially outside of the outer contour in the main emission direction are operated at lower power or deactivated during illumination of the LED pixels,
the illumination device comprises at least a first calibrating mode configured to detect the LED pixels of the emission area that are directed at the non-light-guiding portions of the light guide and a second work operating mode for coupling light into the light guide, and that the control unit is configured to sequentially and/or alternately activate the first and the second operating mode, and
the LED sensor pixels configured to detect reflected radiation occurring in a direction opposite to the main emission direction of the emission area or radiation reflected by non-light-guiding portions of the light guide.

* * * * *